(12) United States Patent
König et al.

(10) Patent No.: US 6,242,657 B1
(45) Date of Patent: Jun. 5, 2001

(54) METHOD FOR PRODUCING AROMATIC NITRO COMPOUNDS

(75) Inventors: Bernd-Michael König, Bergisch Gladbach; Johannes Dühr, Krefeld; Hans-Joachim Raatz, Leverkusen; Manfred Kaczorowski, Bergheim, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/530,204

(22) PCT Filed: Oct. 21, 1998

(86) PCT No.: PCT/EP98/06688

§ 371 Date: Apr. 26, 2000

§ 102(e) Date: Apr. 26, 2000

(87) PCT Pub. No.: WO99/23061

PCT Pub. Date: May 14, 1999

(30) Foreign Application Priority Data

Mar. 2, 1909 (DE) .............................................. 198 08 748
Nov. 3, 1997 (DE) .............................................. 197 48 360

(51) Int. Cl.$^7$ .................................................. C07C 205/00
(52) U.S. Cl. .......................... 568/936; 568/939; 568/940; 568/929; 568/706; 564/441
(58) Field of Search .................... 568/936, 939, 568/940, 929, 706; 564/441

(56) References Cited

U.S. PATENT DOCUMENTS

| | | | |
|---|---|---|---|
| 3,076,037 | 1/1963 | Leib | 260/646 |
| 3,077,502 | 2/1963 | Leib | 260/646 |
| 3,253,045 | 5/1966 | Sparks | 260/646 |
| 4,392,978 | 7/1983 | Elsenbaumer et al. | 252/182 |
| 5,648,565 | 7/1997 | Konig et al. | 568/940 |
| 5,714,647 | 2/1998 | Blank et al. | 568/934 |

FOREIGN PATENT DOCUMENTS

| | | |
|---|---|---|
| 2263218 | 3/1975 | (FR) . |
| 6-293709 | 10/1994 | (JP) . |

OTHER PUBLICATIONS

Ind. Eng. Chem. Res. (month unavailable) 1995, 34, pp. 4297–4309, Modak et al, Role of Interfacial Reaction in Heterogeneous Aromatic Nitration.

Ullmanns Encyklopädie der technischen Chemie, 4, vol. 17, (month unavailable) 1979, pp. 386–387.

Journal of Colloid and Interface Science 158, (month unavailable) 1993, pp. 183–187.

Chhatre et al, Microemulsions as Media for Organic Synthesis: Selective Nitration of Phenol to Ortho–Nitrophenol Using Dilute Nitric Acid.

Faraday Duscuss. Chem. Soc., (month unavailable) 1984, 77, pp. 105–113, Crooks et al, Kinetics of Heterogeneous Nitration in Emulsions.

Ind. Eng. Chem. Res. (Month Unavailable), 1995, vol. 34, pp. 4297–4309, Modak, et al, "Role of Interfacial Reaction in Heterogeneous Aromatic Nitration".

*Primary Examiner*—Samuel Barts
(74) *Attorney, Agent, or Firm*—Joseph C. Gil; Diderico van Eyl

(57) ABSTRACT

In the reaction of aromatic compounds with nitrating acids comprising $HNO_3$ and, if appropriate, $H_2SO_4$ and/or $H_2O$ and/or $H_3PO_4$ to form aromatic nitro compounds, according to the invention an amount of from 0.5 to 20,000 ppm of one or more surface-active substances from the group of the anionic, cationic, zwitterionic or nonionic surface-active substances is added to the reaction mixture.

11 Claims, No Drawings

METHOD FOR PRODUCING AROMATIC NITRO COMPOUNDS

This application is a 371 of PCT/EP98/06688 filed Apr. 26, 2000.

BACKGROUND OF THE INVENTION

The present invention relates to a process for preparing aromatic nitro compounds by reacting aromatic compounds with nitrating acids comprising $HNO_3$ and, if appropriate, $H_2SO_4$ and/or $H_3PO_4$ and/or $H_2O$, the said process being carried out in the presence of surface-active substances.

Nitro compounds of the most varied types are important intermediates for preparing plastics, dyes, auxiliaries, pharmaceuticals and other chemicals.

There is abundant technical and scientific literature, including patent literature, on the preparation of nitro aromatic compounds by various processes involving isothermic or adiabatic conditions, batchwise or continuous operation and various reactors. Products required in small amounts are preferably prepared in batchwise operation, whereas mass products, such as nitrobenzene, nitrotoluene and nitrochlorobenzene, are preferably prepared by continuous operation. Suitable reactors for batchwise operation are, in general, stirred tanks, whereas, for example, tubular reactors are preferred for continuous operation. In the case of products produced in great quantities, there has been no lack of attempts to recover the considerable heat of reaction at a high temperature level and to utilize it for other purposes, for example for concentrating the waste acid. More recent and promising adiabatic operations have been described, inter alia, in EP-A 668 263 and EP-A 675 104. Whereas the processes of the EP patent applications just mentioned already have a high level of successful resource utilization (high material yields and high energy recovery), it is still important, especially for mass products, to attempt to increase resource utilization even more.

In the context of the preparation of 1-nitroanthraquinone, JP 06/293709 mentions the use of di-(2-ethylhexyl)-sulphosuccinic acid Na salt. This process is characterized by a purely organic reaction medium (1,2-dichlorethane) and the use of $NO_2$ or $N_2O_4$ in combination with $SO_3$ as nitrating agent. The di-(2-ethylhexyl)-sulphosuccinic acid Na salt is employed in an amount of 0.17 g, based on the nitrating agent, consisting of 4.1 g of $SO_3$ and 4 g of $NO_2$. The 1- and 2-nitroanthraquinone yield obtained does not exceed that of other examples without the use of the di-(2-ethylhexyl)-sulphosuccinic acid Na salt mentioned. In Ind. Eng. Chem. Res. 34 (1995), 4305, it is noted in the context of an investigation of the role of surface reactions in heterogenic nitrations of aromatic compounds that addition of amphiphilic impurities to the organic phase slows down the reaction; this effect was confirmed using cetyl-trimethylammonium bromide as deactivator (p. 4305, left-hand column, below FIG. 15). In this publication, the reaction conditions involve a mixed acid of 41.41% by weight of $H_2SO_4$, 1% by weight of $HNO_3$ and the remainder to 100% by weight of water. When the reaction is realized on an industrial scale, this phenomenon of reaction slowdown leads to a drastic reduction in the space-time yield.

Surprisingly, it has now been found that, in contrast to the observations in Ind. Eng. Chem. Res., a considerable increase in reaction rate and yield is obtained under the conditions according to the invention described further below when surface-active substances are employed. These surprising results have the following advantages: for mixing the reaction mixture, the expenses required for apparatus are lower, thus reducing the investment costs of a nitration process. The cheap surface-active substances which are prepared as detergents in mass production can be used, in particular. The surface-active substances are employed in the ppm range. It is possible to select surface-active substances having a wide range of properties, and it is likewise possible to select a wide range of other reaction conditions.

DESCRIPTION OF THE INVENTION

The invention relates to a process for preparing aromatic nitro compounds by reacting nitratable aromatic compounds with nitrating acids comprising $HNO_3$ and, if appropriate, $H_2SO_4$ and/or $H_3PO_4$ and/or $H_2O$ at normal to elevated temperature with constant mixing of the aromatic compounds and the nitrating acids, characterized in that the reaction mixture comprises one or more surface-active substances from the group of the anionic, cationic, zwitterionic or nonionic surface-active substances in an amount of from 0.5 to 20,000 ppm.

Surface-active substances which are suitable for the process according to the invention can be from the group of the anionic, cationic, zwitterionic or nonionic surface-active substances. Anionic surface-active substances are, for example, lignosulphonic acids, formaldehyde condensates with aromatically attached sulphonic acid groups, protein condensates, alkanesulphonates, alkylarylsulphonates and alkyl sulphates. Cationic surface-active substances are, for example, the quaternary ammonium salts. Zwitterionic surface-active substances are betaines and sulphobetaines. Nonionic surface-active substances are polyethers which are formed by alkoxylation of compounds having a mobile H atom with ethylene oxide, propylene oxide or butylene oxide, or a mixture of two or more of these. Compounds having a mobile H atom of this type are, for example, alcohols, alkylphenols, phenols, alkylamines, carboxylic acids and carboxamides. Such surfactants, their structure and their preparation are known to the person skilled in the art working in this field.

From among the surface-active substances mentioned, those from the group of the anionic or cationic surface-active substances are preferably suitable for use in the process according to the invention, particularly preferably those from the group of the anionic surface-active substances. Very particularly preferably, these are alkanesulphonates or alkyl sulphates having 10 to 22 C atoms.

It is possible to use a mixture of one or more surface-active substances. The amount of surface-active substances in the reaction mixture at the reactor inlet, for example, is from 0.5 to 20,000 ppm, preferably from 1 to 2000 ppm, particularly preferably front 1 to 200 ppm, very particularly preferably from 5 to 150 ppm.

Surface-active substances from the groups mentioned are suitable for the process according to the invention independently of the degree of their stability. The following configurations are, for example, feasible here:

The surface-active substance or a mixture of two or more surface-active substances is stable and remains in the $HNO_3$-depleted waste acid and becomes reuseable according to the invention during reconcentration and recycling of the waste acid.

The surface-active substance or a mixture of two or more surface-active substances is stable under the reaction conditions according to the invention, but migrates into the organic phase of the aromatic nitro compound and is, during various washing and other treatment processes, removed from the process according to the invention and accordingly has to be replaced, for example at the reactor inlet.

The surface-active substance or a mixture of two or more surface-active substances is not entirely stable under the process conditions according to the invention; it does, however, act in the sense according to the invention during the nitration reaction, but has to be replaced to the extent of its degradation/its destruction.

The surface-active substances can be introduced into the reaction mixture in various ways: Thus, it is possible to feed the surface-active substances into the feed stream of the organic compounds to be nitrated and/or into the feed stream of the nitrating acid. It is also possible to add the surface-active substances to the reaction mixture as a separate feed stream, for example at the reactor inlet.

The nitration process according to the invention which is characterized by the use of surface-active substances can otherwise be applied to all customary processes operating with nitrating acids of $HNO_3$ and optionally $H_2SO_4$ and/or $H_3PO_4$ and/or $H_2O$. Thus, it is possible, for example, to operate under adiabatic or isothermic conditions. Owing to the possibility of energy recovery at a high level, preference is given here to adiabatic conditions. Furthermore, the reaction according to the invention can be carried out continuously or batchwise. Since it is the aim to introduce even products with relatively low tonnages into the more favourable continuous operation, preference is given to this continuous operation.

The process according to the invention can be carried out in all nitration reactors known to the person skilled in the art. Examples which may be mentioned are: the completely back-mixed stirred tank both for batchwise nitrations and in the form of a continuous stirred tank for continuous nitrations; a stirred-tank cascade of, for example, 2 to 5 stirred tanks for continuous nitration; a tubular reactor as reactor for continuous nitrations. All of the reactors mentioned, but in particular the tubular reactor, can be equipped with flow spoiler plates, perforated metal sheets or static mixers.

Owing to the generally greater proportion by volume of the acid phase with respect to the organic phase of the compound to be nitrated, the acid phase is present here as continuous phase, whereas the organic phase of the compound to be nitrated is dispersed in the continuous phase by means of stirrers or dispersion on perforated metal sheets. The nitrating acid and the compound to be nitrated can be combined by simply feeding both substances via pipes to the reactor in which they are then dispersed in the abovementioned manner. However, preference is given to introducing the aromatic compound to be nitrated via one or more nozzles into the nitrating acid, followed by redispersion by means of the stirring described or with the aid of perforated metal sheets, slits and similar devices.

Examples of aromatic compounds to be nitrated which may be mentioned are: benzene, toluene, o-, m- or p-xylene, chlorobenzene, bromobenzene, chlorotoluene, bromotoluene, o-, m-, p-dichlorobenzene, phenol, napthalene, methylnaphthalene, phenol and phenol derivatives and aromatic amines and derivatives thereof. Most of these substances are liquid under reaction conditions. In principle, aromatic compounds which are solid under reaction conditions can also be employed in the process according to the invention; in such cases, an auxiliary solvent is employed to obtain a liquid phase to be nitrated. Preferred aromatic compounds which are nitrated according to the invention are benzene, toluene, chlorobenzene and o-dichlorobenzene.

The nitrating acid used for the nitration comprises $HNO_3$ and, if appropriate, $H_2SO_4$ and/or $H_3PO_4$ and/or water. For aromatic compounds which are readily nitrated, for example for phenols, a nitrating acid is used which comprises $HNO_3$ and, if appropriate, $H_2O$. In cases of a mixed nitrating acid ($HNO_3$, $H_2SO_4$ and, if appropriate, $H_2O$) the $H_2SO_4$ is on some occasions completely or partially replaced by $H_3PO_4$ to influence isomer distribution. Such nitrating acids may additionally comprise one or more of the abovementioned surface-active substances. In most industrially relevant cases, the nitrating acid comprises $HNO_3$, $H_2SO_4$ and, if appropriate, a remainder to 100% by weight of $H_2O$ and, if appropriate, one or more surface-active substances. The nitrating acid preferably comprises $H_2O$. For nitrations which are carried out isothermally, the nitrating acids used in most cases comprise 20 to 40% by weight of $HNO_3$, 49 to 60% by weight of $H_2SO_4$ and 11 to 20% by weight of $H_2O$ (Ullmanns Encyklopädie der technischen chemie, 4, Aufl., Vol. 17, p. 386 (1979)). For adiabatic processes, use is made of nitrating acids comprising 1 to 8% by weight, preferably 2 to 6% by weight, particularly preferably from 2.5 to 5% by weight, of $HNO_3$ and 56–85% by weight, preferably 64 to 79% by weight, of $H_2SO_4$. The remainder to 100% by weight is water. All percentages are based on the total weight of $H_2SO_4$, $HNO_3$ and $H_2O$.

The reactants are mixed in the wide range from 20 to 160° C. In a manner known to the person skilled in the art, aromatic compounds which are more sensitive to undesirable subsequent nitration and oxidation are mixed in a lower section of this range, for example at from 20 to 110° C., preferably from 30 to 100° C., particularly preferably from 40 to 90° C. One such sensitive aromatic compound is, for example, toluene. In the case of aromatic compounds which are less sensitive to multiple nitration and oxidation, mixing is carried out in an elevated section of the range mentioned, for example at from 60 to 160° C., preferably from 70 to 140° C., particularly preferably from 80 to 120° C. Such less sensitive aromatic compounds are, for example, chlorobenzene, bromobenzene, dichlorobenzenes. If the nitration is carried out isothermally, the mixing temperature is maintained by suitable cooling devices. If the nitration is carried out adiabatically, the resulting exothermic heat of reaction is not dissipated, but remains in the reaction mixture and may serve, in a manner that is likewise known, for concentrating the waste nitrating acid after phase separation. Such concentrating is generally carried out by flash evaporation of the waste acid under reduced pressure. In many cases, the $H_2SO_4$ concentration in this waste acid is re-established completely, and the waste acid can then, after the $HNO_3$ that has been consumed has been replaced, be used once more as nitrating acid in the process according to the invention. However, in any case at least partial concentration of the $H_2SO_4$ in the waste acid is achieved.

The molar ratio of the aromatic compound to be nitrated to $HNO_3$ in the nitrating acid is generally from 0.9 to 1.5:1. To minimize formation of undesirable polynitrated aromatic compounds, the molar ratio of aromatic compound to $HNO_3$ is preferably from 1.0 to 1.5:1, particularly preferably from 1.03 to 1.3:1, very particularly preferably from 1.05 to 1.2:1. However, if the aromatic nitro compounds obtainable according to the invention are to be subjected to dinitration, the extended range, starting at 0.9 mol of aromatic compound to 1 mol of $HNO_3$, is also permissible.

The process according to the invention results in shorter reaction times and higher yields of the desired aromatic nitro compound. Furthermore, the higher yields are associated with higher selectivity, i.e. suppression of undesirable by-products.

A specific variant of the nitration process according to the invention in the presence of surface-active substances relates to the preparation of mononitrotoluenes.

The specific variant accordingly relates to a process for the continuous or batchwise preparation of mononitrotoluenes by reacting toluene with an $HNO_3/H_2SO_4/H_2O$ mixture in the presence of from 0.5 to 20,000 ppm of one or more surface-active substances with formation, essentially, of the mononitrotoluenes and reaction water, characterized by the steps a) feeding of the reaction participants toluene, $HNO_3$, $H_2SO_4$, $H_2O$ and surface-active substances in any sequence into a reactor equipped with mixing elements, in which a1) the amount of $HNO_3$ is 1–8% by weight, the amount of $H_2SO_4$ is 56 to 85, preferably 58 to 74% by weight and the amount of $H_2O$ is the remainder to 100% by weight and 100% by weight signifies the sum of $HNO_3+H_2SO_4+H_2O$, a2) the $H_2O$ is used as such, as dilution $H_2O$ of the $HNO_3$, as dilution $H_2O$ of the $H_2SO_4$ or in a plurality of the said forms and a3) the molar ratio of toluene to $HNO_3$ is 0.9–1.5, b) rapid and intensive mixing of the totality of the reaction participants, using a mixing energy of 1 to 80 watts per liter of the total reaction mixture, preferably 1 to 70 W/l, particularly preferably 1 to 60 W/l, very particularly preferably 5 to 50 W/l, c) carrying out the reaction under adiabatic conditions, the reaction participants being fed in at temperatures such that the mixing proceeds in the range from 20–120° C., preferably from 30–110° C., particularly preferably from 40–100° C., and the temperature at the end of tie reaction does not exceed 135° C., d) separating the reaction mixture, after carrying out the reaction, into an organic and an inorganic phase and e) work-up of the substantially $HNO_3$-free inorganic phase by distillation with removal of water, where the inorganic phase, if appropriate, comprises the surface-active substance(s).

These variants are carried out batchwise or continuously, preferably continuously.

The continuous procedure can be carried out, for example, in the following manner: the reaction participants are rapidly mixed in their total amount in a mixing element and fed into a reactor as a mixture. The mixing time with the continuous procedure is generally less than 3 sec., for example 1 msec. to 2.99 sec., preferably 1 msec. to 2 sec. The reactor is insulated if required, substantially prevents back-mixing and is operated adiabatically. For the substantial prevention of back-mixing, the reactor is subdivided or is composed of a plurality of chambers or units; at the transitions between the reactor parts, the reaction mixture is redispersed. The mixture reacted to exhaustion runs off and is separated in a separation vessel; the separation proceeds rapidly. The organic phase is worked-up in a conventional manner, e.g. by washing and distillation, or is immediately fed to a second nitration. Generally, in particular when there is an excess of toluene, the inorganic phase separated off is virtually free of nitric acid. If this is not the case, in particular when there is an excess of nitric acid, residual nitric acid can be consumed in a post-reactor with addition of further toluene in the sense of a reactive extraction. The inorganic acid phase substantially freed of nitric acid is preferably fed to a flash evaporation with utilization of the heat of reaction absorbed and under reduced pressure. In this case, water is removed from the acid and, preferably, simultaneously, the acid is brought to the input concentration and the input temperature. This acid is then, as $H_2SO_4$, directly suitable for use in step a) and comprises, if appropriate, the surface-active substance(s). This return of the worked-up inorganic phase ($H_2SO_4$, $H_2O$) to the process results in a circulation procedure for the $H_2SO_4$ and, if appropriate, the surface-active substance(s); it can be expedient to eject a small part of this $H_2SO_4$ to keep any contamination to a low level. In the event that the inorganic phase still contains toluene, nitrotoluene and any organic by-products, it can be expedient to strip the inorganic phase before the flash evaporation to remove the organic compounds. The water obtained subsequently as flash condensate is then of higher purity and its disposal is simpler. Obviously, the flash condensate can also be freed of organic compounds, e.g. by stripping or phase separation, a residual flash condensate and a high-purity water-acid phase similarly remaining. The organic compounds arising in the post-reaction of the $HNO_3$ with further toluene and in the stripping or other separations, such as phase separation, can be added to the process at a suitable point (toluene, (di) nitrotoluene) or are ejected and disposed of (impurities, by-products).

The reaction participants can be fed to the reactor equipped with mixing elements together, but also individually or as mixtures of two or three thereof simultaneously or successively. The feedstocks can be mixed, for example, in such a way that toluene and nitric acid or, it required, water are simultaneously or successively added as separate streams to the concentrated recycled sulphuric acid, in which case the nitric acid can be diluted by water and/or sulphuric acid and water. Toluene can also be premixed with water and sulphuric acid and the resulting emulsion is further intensively mixed with nitric acid which can be mixed with sulphuric acid and/or water. Furthermore, the toluene can also be intensively mixed with a nitrating acid of sulphuric acid, nitric acid and water and then further treated according to the invention. The surface-active substance(s) to be employed according to the invention can be added to any of these streams or stream mixtures or employed separately. Still other variants of the feeding of the reaction participants, their intensive mixing and further treatment are easily recognizable to the person skilled in the art. For this purpose, mixing elements known in the art are suitable, e.g.: 1. static mixers, 2. pumps, 3. nozzles, 4. agitators or combinations thereof.

For the reaction to succeed, it is of little importance in which sequence and combination the reaction participants nitric acid and toluene as well as sulphuric acid and water and the surface-active substance(s) are mixed together, as long as the reaction mixture has the composition according to the invention after the total mixing and the mixing takes place at the intensity according to the invention and, when the reaction is carried out continuously, substantially free from back-mixing.

The mixing intensity, in the case of the batchwise procedure, apart from the high energy input, can also be characterized by the short reaction participant addition time which is 0.001 to 15%, preferably 0.001 to 3%, of the time which is required for the course of the reaction between toluene and nitric acid. It is thus also possible to carry out the process according to the invention batchwise in a stirred tank.

The feeding and intensive mixing of the reaction participants are followed, in the continuous procedure, by at least two redispersions. For this purpose, in the reactor there are present, preferably in sections, static mixer elements, if required also in the form of spherically shaped fixed internals, such as perforated metal sheets, slotted metal sheets, impact baffles, vanes or agitators or similar internals or elements known for this purpose to the person skilled in the art.

Continuously operated reactors for the specific variant which can be mentioned by way of example are as follows: tubular reactors having internals for redispersion, such as vanes, deflection baffles, static mixers or agitators and the like; intensively stirred tanks in a cascade arrangement; loop reactors having internals as above; combinations of a plurality of the said apparatuses; other reactors of equivalent action, such as chamber reactors with agitators in each chamber. Tubular reactors having internals are preferably used. The internals are preferably perforated metal sheets. All internals represent subdivisions of the entire apparatus which equally serve for the redispersion and the substantial prevention of back-mixing.

After the intensive mixing, after each dispersion or after the mixture has flowed through a certain part-length of the reactor, coalescence of the dispersion droplets is observed which can be reversed by redispersion. The number of redispersion operations is, according to the invention, 2 to 50, preferably 3 to 30, particularly preferably 4 to 20. To overcome the pressure drops occurring in this case, a mixing energy of 1 to 80 watts/liter, preferably 1 to 70 W/l, particularly preferably 1 to 60 W/l, very particularly preferably 5 to 50 W/l, per liter of the total reaction mixture is added to the reaction system with the reaction participants.

The reaction participants are mixed in the specific variant in the range from 20 to 110° C., preferably from 30 to 110° C., particularly preferably from 40 to 110° C. Adiabatic reaction conditions are maintained. The final temperature is dependent on the height of the mixing temperature, on the ratios of the amounts of the reaction participants and on the conversion rate; it generally does not exceed 135° C. and usually does not exceed 125° C.

The content of added nitric acid in the reaction mixture at the time of mixing in the specific variant, based oil the sum of nitric acid, sulphuric acid and water, is 1 to 8% by weight, preferably 1 to 6% by weight, particularly preferably 1.5 to 4% by weight. Nitric acid can be used in highly concentrated form or as an azeotrope, but preferably in the form of the inexpensive "weak acid", having approximately 60–65% by weight.

The content of sulphuric acid in the reaction mixture at the time of mixing in the specific variant, based on the sum of nitric acid, sulphuric acid and water, is 56–85% by weight, preferably 58–74% by weight, particularly preferably 60–72% by weight, very particularly preferably 61–69% by weight. These figures do not include any process-specific impurities which may be contained in the event of an $H_2SO_4$ circulation procedure.

The amount of one or more surface-active substances is that specified above. The remainder to 100% by weight is $H_2O$. This can be used as such, as dilution $H_2O$ of the $H_2SO_4$, as dilution $H_2O$ of the $HNO_3$ or in a plurality of the said forms. $H_2O$ is preferably present as dilution $H_2O$ of both the $H_2SO_4$ and of the $HNO_3$.

Since the intensity of nitration with changing contents of nitric acid in the nitrating acid is dependent on the ratio of sulphuric acid to water, it is determined and, if required, adjusted on the basis of the sulphuric acid concentration of the outflowing and substantially nitric acid-free spent acid. This $H_2SO_4$ concentration of the spent acid is to be, according to the invention, 62 to 74% by weight, preferably 64 to 72% by weight, particularly preferably 66 to 70% by weight.

For reuse, the outflowing sulphuric acid is concentrated by 0.6–7 percentage points, in many cases by 1.5–3 percentage points, water (reaction water, possibly dilution water) being ejected by distillation. For this purpose the heat of reaction absorbed from the outflowing $H_2SO_4$ owing to the adiabatic reaction conditions is preferably utilized and reduced pressure in the range from 1 to 100 mbar, preferably from 5–80 mbar, particularly preferably from 10–75 mbar, is employed. This can be carried out, for example, in the form of a flash evaporation. The $H_2SO_4$ recovered in this case is suitable for use in step a). The ejection of water by distillation is preferably carried out in such a way that the temperature and concentration of the concentrated $H_2SO_4$ are directly equivalent to the values demanded in step a). Such a utilization of the heat of reaction makes the process according to the invention more economical than the known processes for the preparation of nitrotoluenes.

Possible embodiments with respect to the nitrating acids having varying compositions, to outflowing $H_2SO_4$ concentrations, temperature conditions and pressure of the flash evaporation and degree of concentration of the $H_2SO_4$ may be summarized by way of example as follows, without mentioning the surface-active substance(s), (cases a, b and c):

| Nitrating acid | a | b | c |
|---|---|---|---|
| $HNO_3$ (% by weight) | 4.00 | 3.00 | 2.50 |
| $H_2SO_4$ (% by weight) | 64.11 | 65.56 | 66.79 |
| $H_2O$ (% by weight) | 31.89 | 31.44 | 30.71 |
| Strength of the acids used | | | |
| $HNO_3$ (% by weight) | 60.0 | 60.0 | 60.0 |
| $H_2SO_4$ (% by weight) | 68.69 | 69.01 | 69.69 |
| Outflowing $H_2SO_4$ (% by weight) | 66.0 | 67.0 | 68.0 |
| Mixing temperature (° C.) | 80 | 85 | 90 |
| Final temperature (° C.), approximately | 120 | 115 | 115 |
| Pressure in flash evaporation (approximate mbar) | 40 | 50 | 60 |

The molar ratio of toluene to $HNO_3$ is generally 0.9–1.5. In order to minimize the formation of undesirable dinitrotoluenes, the molar ratio of toluene to nitric acid is preferably 1.0 to 1.5, particularly preferably 1.03 to 1.3, very particularly preferably 1.05 to 1.2. However, if the nitrotoluenes available according to the invention are to be fed to the dinitration, other molar ranges, e.g. 0.9–1.2 mol, preferably 0.9–1.05 mol, particularly preferably 0.95–1 mol, of toluene per mole of nitric acid are also permissible.

The reaction of the process according to the invention proceeds according to the formula:

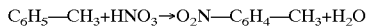

$$C_6H_5—CH_3 + HNO_3 \rightarrow O_2N—C_6H_4—CH_3 + H_2O$$

Thus toluene and $HNO_3$ are introduced into the process and mononitrotoluene and reaction water are ejected, while the $H_2SO_4/H_2O$ mixture described, which, if appropriate, contains the surface-active substance(s), represents the reaction medium.

Since, when the process is carried out industrially, dilute nitric acids are advantageously used, depending on the prices of the nitric acids respectively available, additionally to the reaction water, dilution $H_2O$ of the $HNO_3$ must also be ejected.

The organic phase arising in the separation of the reaction mixture can be worked up to give pure mononitrotoluene or be fed to the dinitrotoluene preparation. In the former case at least molar amounts of toluene or a slight molar excess is used, as described above, in order not only to consume the $HNO_3$ but also to repress the second nitration; any toluene excess is distilled off from the organic phase separated off. Before this, the organic phase can be washed in order to separate off water-, acid- or alkali-soluble impurities, such as inorganic and organic acids and phenolic impurities. However, the formation of oxidation products (phenols, oxidation of the $CH_3$ group) is strongly suppressed in the process according to the invention. Likewise, the formation of dinitrotoluenes is highly repressed. However, these dinitrotoluenes are not an interference if a second nitration is in any case intended; therefore, in such cases, the procedure may also be carried out with a toluene deficiency.

A further specific variant of the nitration process according to the invention in the presence of surface-active substances relates to the preparation of mononitrohalogenobenzenes.

The second specific variant accordingly relates to a process for the continuous or batchwise preparation of mononitrohalogenobenzenes by reacting halogenobenzenes with an $HNO_3/H_2SO_4/H_2O$ mixture in the presence of from 0.5 to 20,000 ppm of one or more surface-active substances with formation, essentially, of the mononitrohalogenobenzenes and reaction water, characterized by the steps a) feeding of the reaction participants halogenobenzene, $HNO_3$, $H_2SO_4$ and $H_2O$ in any sequence into a reactor equipped with mixing elements, in which
  a1) the amount of $HNO_3$ is from 1 to 8% by weight, the amount of $H_2SO_4$ is 56 to 85% by weight and the amount of $H_2O$ is the remainder to 100% by weight and 100% by weight signifies the sum of $HNO_3+H_2SO_4+H_2O$,
  a2) the $H_2O$ is used as such, as dilution $H_2O$ of the $HNO_3$, as dilution $H_2O$ of the $H_2SO_4$ or in a plurality of the said forms and
  a3) the molar ratio of halogenobenzene to $HNO_3$ is 0.9–1.5,
b) rapid and intensive mixing of the totality of the reaction participants, using a mixing energy of 1 to 80 watts per liter of the total reaction mixture, preferably 1 to 70 W/l, particularly preferably 1 to 60 W/l, very particularly preferably 5 to 50 W/l,
c) carrying out the reaction under adiabatic conditions, the reaction participants being fed in at temperatures such that the mixing proceeds in the range from 60 to 160° C. and the temperature at the end of the reaction does not exceed 180° C.,
d) separating the reaction mixture, after carrying out the reaction, into an organic and an inorganic phase and
e) work-up of the substantially $HNO_3$-free inorganic phase by distillation with removal of water, where the inorganic phase, if appropriate, comprises the surface-active substance(s).

For the purpose of the invention, halogenobenzenes are chlorobenzene, o-, m-, p-dichlorobenzene, o-, m-, p-chlorotoluene and bromobenzene, preferably chlorobenzene and o-, m-, p-dichlorobenzene, particularly preferably chlorobenzene and o-dichlorobenzene.

This variant, too, can be carried out continuously or batchwise, preferably continuously. For continuous operation, the procedure of the first specific variant can be followed, using halogenobenzene instead of toluene.

In the second specific variant, the reaction participants are mixed in the range from 60 to 160° C., preferably from 70 to 140° C., particularly preferably from 80 to 120° C. Adiabatic reaction conditions are maintained. The final temperature is dependent on the height of the mixing temperature, on the ratios of the amounts of the reaction participants and on the conversion rate; it generally does not exceed 180° C. and usually does not exceed 160° C.

The content of added nitric acid in the reaction mixture at the time of mixing, based on the sum of nitric acid, sulphuric acid and water, is 1 to 8% by weight, preferably 2 to 6% by weight, particularly preferably 2.5 to 5% by weight, in the second specific variant.

The content of sulphuric acid in the reaction mixture at the time of mixing, based on the sum of nitric acid, sulphuric acid and water, is 56 to 85% by weight, preferably 56.5 to 84.5% by weight, particularly preferably 65 to 79% by weight, very particularly preferably 67.5 to 77% by weight, in the second specific variant.

The remainder to 100% is $H_2O$.

According to the invention, the $H_2SO_4$ concentration of the spent acid in the second specific variant should be 60 to 85% by weight, preferably 68 to 80% by weight, particularly preferably 70 to 78% by weight. For reuse, the outflowing sulphuric acid is concentrated by 0.6 to 7.5 percentage points, in many cases by 1.7 to 4.2 percentage points. For this purpose the heat of reaction absorbed from the outflowing $H_2SO_4$ is utilized and reduced pressure, for example from 40 to 150 mbar, preferably from 40 to 120 mbar, particularly preferably from 50–100 mbar, is employed. Here, too, this can be carried out, for example, in the form of a flash evaporation.

Possible embodiments with respect to the nitrating acids having varying compositions, to outflowing $H_2SO_4$ concentrations, temperature conditions and pressure of the flash evaporation and degree of concentration of the $H_2SO_4$ may be summarized by way of example for the second specific variant as follows, likewise without mentioning the surface-active substance(s) (cases a and c: chlorobenzene; case b: o-dichlorobenzene):

| Nitrating acid | a | b | c |
|---|---|---|---|
| $HNO_3$ (% by weight) | 3.00 | 3.00 | 5.00 |
| $H_2SO_4$ (% by weight) | 68.50 | 74.37 | 67.50 |
| $H_2O$ (% by weight) | 28.50 | 22.63 | 27.50 |
| Strength of the acids used | | | |
| $HNO_3$ (% by weight) | 60.00 | 60.00 | 60.00 |
| $H_2SO_4$ (% by weight) | 72.11 | 78.28 | 73.64 |
| Outflowing $H_2SO_4$ (% by weight) | 70.00 | 76.00 | 70.00 |
| Mixing temperature (° C.) | 110 | 110 | 100 |
| Final temperature (approximately ° C.) | 140 | 140 | 150 |
| Pressure in flash evaporation (approximately mbar) | 95 | 48 | 60 |

The molar ratio of halogenobenzene to $HNO_3$ is generally 0.9 to 1.5. In order to minimize the formation of undesirable dinitrohalogenobenzenes, the molar ratio of halogenobenzene to nitric acid is preferably 1.0 to 1.5, particularly preferably 1.01 to 1.3, very particularly preferably 1.05 to 1.2. However, if the nitrohalogenobenzenes available according to the invention are to be fed to the dinitration, other ranges, e.g. 0.9 to 1.2 mol, preferably 0.9 to 1.05 mol, particularly preferably 0.95 to 1 mol, of halogenobenzene per mole of nitric acid are also permissible.

The reaction of the process according to the invention proceeds according to the formula:

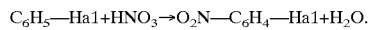

The organic phase arising in the separation of the reaction mixture can be worked analogously to the first specific variant.

The invention is further described in the following illustrative examples in which all parts and percentages are by weight unless otherwise indicated.

EXAMPLE 1

At 75° C., a stream consisting of 187.8 kg of $H_2SO_4$ (70%)/h and 8.7 kg of $HNO_3$ (67%)/h and a stream of 9.4 kg of toluene/h were fed simultaneously into a tubular reactor having perforated plates as redispersing elements. The nitrating acid contained 25 ppm of alkanesulphonate ($C_{12}$–$C_{18}$). After a residence time of about 35 sec., the mixture reacted to exhaustion left the reactor. Phase separation gave:

| | |
|---|---|
| Organic phase: | 12.92 kg/h |
| of the following composition (calibrated GC): | |
| Toluene: | 6.41% |
| o-Nitrotoluene: | 54.06% |
| m-Nitrotoluene: | 5.36% |
| p-Nitrotoluene: | 33.38% |
| 2,4-Dinitrotoluene: | 0.19% |
| 2,6-Dinitrotoluene: | 0.07% |
| Dinitro-o-cresol: | 0.14% |
| Dinitro-p-cresol: | 0.40% |
| Acid phase: | 121 ltr/h |
| with 4.30 g of mononitrotoluenes per ltr of acid phase. | |

This corresponds to a yield of mononitrotoluenes of 98.6% of the theoretical yield.

EXAMPLE 2

Comparative Example

At 75° C., a stream consisting of 187.8 kg of $H_2SO_4$ (70%)/h and 8.7 kg of $HNO_3$ (67%)/h and a stream of 9.4 kg of toluene/h were fed simultaneously into a tubular reactor having perforated plates as redispersing elements; alkanesulphonate was not employed. After a residence time of about 35 sec., the mixture reacted to exhaustion left the reactor. Phase separation gave:

| | |
|---|---|
| Organic phase: | 12.40 kg/h |
| of the following composition (calibrated GC): | |
| Toluene: | 15.54% |
| o-Nitrotoluene: | 48.65% |
| m-Nitrotoluene: | 4.91% |
| p-Nitrotoluene: | 30.00% |
| 2,4-Dinitrotoluene: | 0.29% |
| 2,6-Dinitrotoluene: | 0.11% |
| Dinitro-o-cresol: | 0.10% |
| Dinitro-p-cresol: | 0.39% |
| Acid phase: | 121 ltr/h |
| with 3.80 g of mononitrotoluenes per ltr of acid phase. | |

This corresponds to a yield of mononitrotoluenes of 85.4% of the theoretical yield.

EXAMPLE 3

At 75° C., a stream consisting of 187.8 kg of $H_2SO_4$ (70%)/h and 8.7 kg of $HNO_3$ (67%)/h and a stream of 9.4 kg of toluene/h were fed simultaneously into a tubular reactor having perforated plates as redispersing elements. The nitrating acid contained 33 ppm of benzyltrimethylammonium chloride. After a residence time of about 35 sec., the mixture reacted to exhaustion left the reactor. Phase separation gave:

| | |
|---|---|
| Organic phase: | 12.80 kg/h |
| of the following composition (calibrated GC): | |
| Toluene: | 7.00% |
| o-Nitrotoluene: | 54.02% |
| m-Nitrotoluene: | 5.39% |
| p-Nitrotoluene: | 32.91% |
| 2,4-Dinitrotoluene: | 0.15% |
| 2,6-Dinitrotoluene: | 0.05% |
| Dinitro-o-cresol: | 0.12% |
| Dinitro-p-cresol: | 0.36% |
| Acid phase: | 121 ltr/h |
| with 4.20 g of mononitrotoluenes per ltr of acid phase. | |

This corresponds to a yield of mononitrotoluenes of 97.3% of the theoretical yield.

EXAMPLE 4

At 110° C., a stream consisting of 187.8 kg of $H_2SO_4$ 70%/h and 8.7 kg of $HNO_3$ 67%/h and a stream of 11.5 kg of chlorobenzene/h were fed simultaneously into a tubular reactor equipped with perforated plates as redispersing elements. The nitrating acid contained 100 ppm of alkane sulphonate. After a residence time of about 35 sec., the mixture reacted to exhaustion left the reactor.

Phase separation gave:

| | |
|---|---|
| Organic phase: | 14.30 kg/h |
| of the following composition (calibrated GC): | |
| Chlorobenzene | 7.20% |
| o-Nitrotoluene: | 36.19% |
| m-Nitrotoluene: | 1.64% |
| p-Nitrotoluene: | 54.97% |
| Acid phase: | 121 ltr/h |
| with 5.4 g of mononitrochlorobenzenes per ltr of acid phase. | |

This corresponds to a yield of mononitrochlorobenzenes of 98.2% of the theoretical yield.

EXAMPLE 5

Comparative Example

At 110° C., a stream consisting of 187.8 kg of $H_2SO_4$ 70%/h and 8.7 kg of $HNO_3$ 67%/h and a stream of 11.5 kg of chlorobenzene/h were fed simultaneously into a tubular reactor equipped with perforated plates as redispersing elements; alkane sulphonate was not employed. After a residence time of about 35 sec., the mixture reacted to exhaustion left the reactor.

Phase separation gave:

| | |
|---|---|
| Organic phase: | 13.9 kg/h |
| of the following composition (calibrated GC): | |
| Chlorobenzene | 15.53% |
| o-Nitrotoluene: | 32.86% |
| m-Nitrotoluene: | 1.47% |
| p-Nitrotoluene: | 50.14% |
| Acid phase: | 121 ltr/h |
| with 5.1 g of mononitrochlorobenzenes per ltr of acid phase. | |

This corresponds to a yield of mononitrochlorobezenes of 87.3% of the theoretical yield.

EXAMPLE 6

At 75° C., a stream consisting of 187.8 kg of $H_2SO_4$ 70%/h and 8.7 kg of $HNO_3$ 67%/h and a stream of 9.4 kg of toluene/h were fed simultaneously into a tubular reactor equipped with perforated plates as redispersing elements. The mixed acid contained 25 ppm of alkyl sulphate. After a residence time of about 35 sec., the mixture reacted to exhaustion left the reactor.

Phase separation gave:

| | |
|---|---|
| Organic phase: | 12.85 kg/h |
| of the following composition | |
| (calibrated GC): | |
| Toluene: | 6.57% |
| o-Nitrotoluene: | 53.94% |
| m-Nitrotoluene: | 5.35% |
| p-Nitrotoluene: | 32.30% |
| 2,4-Dinitrotoluene: | 0.25% |
| 2,6-Dinitrotoluene: | 0.11% |
| Dinitro-o-cresol: | 0.12% |
| Dinitro-p-cresol: | 0.36% |
| Acid phase: | 121 ltr/h |
| with 4.20 g of mononitrotoluenes | |
| per ltr of acid phase. | |

This corresponds to a yield of mononitrotoluenes of 98.5% of theory.

Although the present invention has been described in detail with reference to certain preferred versions thereof, other variations are possible. Therefore, the spirit and scope of the appended claims should not be limited to the description of the versions contained therein.

What is claimed is:

1. Process for preparing aromatic nitro compounds comprising the step of reacting a nitratable aromatic compound with nitrating acids comprising $HNO_3$ at a normal to elevated temperature with constant mixing of the aromatic compound and the nitrating acids, wherein the reaction mixture comprises one or more surface-active substances comprising a member selected from the group consisting of anionic, cationic, zwitterionic nonionic surface-active substances in an amount of from 0.5 to 20,000 ppm.

2. Process according to claim 1, wherein the content of one or more surface-active substances is from 1 to 2000 ppm.

3. Process according to claim 1, wherein the one or more surface-active substances employed comprise a member selected from the group consisting of anionic and cationic surface-active substances.

4. Process according to claim 1, wherein the reaction is carried out under adiabatic or isothermic conditions.

5. Process according to claim 1, wherein the reaction is carried out continuously or batchwise.

6. Process according to claim 1, wherein the reactor used for the reaction is a stirred tank, a stirred tank cascade or a tubular reactor, which can be equipped with flow spoiler plates, perforated metal sheets or static mixers.

7. Process according to claim 1, wherein the aromatic compound is introduced via one or more nozzles into the nitrating acid.

8. Process according to claim 1, wherein the aromatic compound reacted comprises a member selected from the group consisting of benzene, toluene, o-xylene, m-xylene, p-xylene, chlorobenzene, bromobenzene, chlorotoluene, bromotoluene, o-dichlorobenzene, m-dichlorobenzene, and p-dichlorobenzene, naphthalene, methylnaphthalene, phenol, phenol derivatives, aromatic amines and derivatives.

9. The method of claim 1, wherein the step of reacting the nitratable aromatic compound with the nitrating acids is carried out with a member selected from the group consisting of $H_2SO_4$, $H_2O$ and $H_3PO_4$.

10. Process for the continuous or batchwise preparation of mononitrotoluenes by reacting toluene with an $HNO_3/H_2SO_4/H_2O$ mixture in the presence of from 0.5 to 20,000 ppm of one or more surface-active substances with formation, essentially, of the mononitrotoluenes and reaction water the process comprising the steps of a) feeding of the reaction participants toluene, $HNO_3$, $H_2SO_4$, $H_2O$ and surface-active substances in any sequence into a reactor equipped with mixing elements, in which a1) the amount of $HNO_3$ is 1–8% by weight, the amount of $H_2SO_4$ is 56 to 85% by weight and the amount of $H_2O$ is the remainder to 100% by weight and 100% by weight signifies the sum of $HNO_3 + H_2SO_4 + H_2O$, a2) the $H_2O$ is used as such, as dilution $H_2O$ of the $HNO_3$, as dilution $H_2O$ of the $H_2SO_4$ or in a plurality of the said forms and a3) the molar ratio of toluene to $HNO_3$ is 0.9–1.5, b) rapid and intensive mixing of the totality of the reaction participants, using a mixing energy of 1 to 80 watts per liter of the total reaction mixture, c) carrying out the reaction under adiabatic conditions, the reaction participants being fed in at temperatures such that the mixing proceeds in the range from 20–120° C. and the temperature at the end of the reaction does not exceed 135° C., d) separating the reaction mixture, after carrying out the reaction, into an organic and an inorganic phase and e) work-up of the substantially $HNO_3$-free inorganic phase by distillation with removal of water, where the inorganic phase, if appropriate, comprises the surface-active substances.

11. Process for the continuous preparation of mononitro-halogenobenzenes by reacting halogenobenzenes with an $HNO_3/H_2SO_4/H_2O$ mixture in the presence of from 0.5 to 20,000 ppm of one or more surface-active substances with formation, essentially, of the mononitrohalogenobenzenes and reaction water, the process comprising the steps of a) feeding of the reaction participants halogenobenzene, $HNO_3$, $H_2SO_4$, $H_2O$ and surface-active substances in any sequence into a reactor equipped with mixing elements, in which a1) the amount of $HNO_3$ is from 1 to 8% by weight, the amount of $H_2SO_4$ is 56 to 85% by weight and the amount of $H_2O$ is the remainder to 100% by weight and 100% by weight signifies the sum of $HNO_3 + H_2SO_4 + H_2$, a2) the $H_2O$ is used as such, as dilution $H_2O$ of the $HNO_3$, as dilution $H_2O$ of the $H_2SO_4$ or in a plurality of the said forms and a3) the molar ratio of halogenobenzene to $HNO_3$ is 0.9–1.5, b) rapid and intensive mixing of the totality of the reaction participants, using a mixing energy of 1 to 80 watts per liter of the total reaction mixture, c) carrying out the reaction under adiabatic conditions in reactors which substantially prevent the back-mixing of the reaction participants and in which the reaction participants are redispersed at least 2 times whilst flowing through the reactor, the reaction participants being fed in at temperatures such that the mixing proceeds in the range from 60 to 160° C. and the temperature at the end of the reaction does not exceed 180° C., d) separating the reaction mixture, after carrying out the reaction, into an organic and an inorganic phase and e) work-up of the substantially $HNO_3$-free inorganic phase by distillation with removal of water, where the inorganic phase, if appropriate, comprises the surface-active substances.

* * * * *